United States Patent [19]

Stuk et al.

[11] Patent Number: 5,569,777
[45] Date of Patent: Oct. 29, 1996

[54] PROCESS FOR THE PREPARATION OF A SUBSTITUTED 2,5-DIAMINO-3-HYDROXYHEXANE

[75] Inventors: Timothy L. Stuk, Lindenhurst; Anthony R. Haight, Mundelein; Howard E. Morton; Timothy A. Robbins, both of Gurnee; David Scarpetti, Evanston; Jien-Heh J. Tien, Libertyville, all of Ill.

[73] Assignee: Abbott Laboratories, Abbott Park, Ill.

[21] Appl. No.: 418,727

[22] Filed: Apr. 7, 1995

Related U.S. Application Data

[60] Division of Ser. No. 281,502, Jul. 27, 1994, Pat. No. 5,491,253, which is a continuation-in-part of Ser. No. 141,795, Oct. 22, 1993, abandoned.

[51] Int. Cl.$^6$ .................. C07C 261/00; C07C 233/00; C07D 209/04
[52] U.S. Cl. .................. 560/24; 564/164; 548/469; 548/491; 546/98
[58] Field of Search .................. 560/24; 564/164; 548/469, 491; 546/98

[56] References Cited

FOREIGN PATENT DOCUMENTS 486948  1/1992  European Pat. Off. .

OTHER PUBLICATIONS

Ghosh A et al J Org Chem (1993) 58(5) 1025–9.

*Primary Examiner*—Paul J. Killos
*Attorney, Agent, or Firm*—Steven R. Crowley

[57] ABSTRACT

Intermediates and processes are disclosed which are useful for the preparation of a substantially pure compound of the formula:

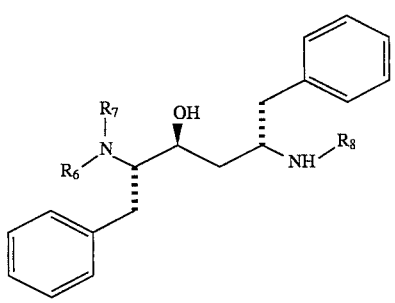

wherein $R_6$ and $R_7$ are each hydrogen or $R_6$ and $R_7$ are independently selected from

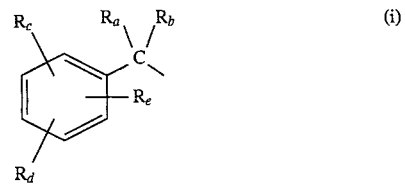

(i)

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

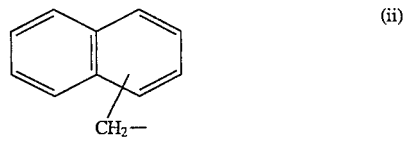

(ii)

wherein the naphthyl ring is unsubstituted or substituted with one, two or three substitutents independently selected from loweralkyl, trifluoromethyl, alkoxy and halo; or $R_6$ is as defined above and $R_7$ is $R_{7a}OC(O)$— wherein $R_{7a}$ is loweralkyl or benzyl; or $R_6$ and $R_7$ taken together with the nitrogen atom to which they are bonded are

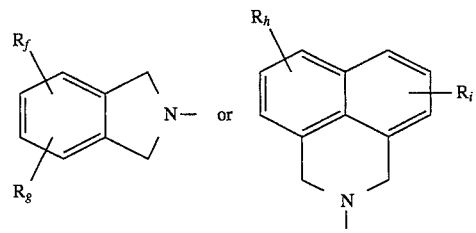

wherein $R_f$, $R_g$, $R_h$ and $R_i$ are independently selected from hydrogen, loweralkyl, alkoxy, halogen and trifluoromethyl and $R_8$ is hydrogen or —C(O)R" wherein R" is loweralkyl, alkoxy, benzyloxy or phenyl wherein the phenyl ring is unsubstituted or substituted with one, two or three substituents independently selected from loweralkyl, trifluoromethyl, alkoxy and halo; or an acid addition salt thereof.

2 Claims, No Drawings

PROCESS FOR THE PREPARATION OF A SUBSTITUTED 2,5-DIAMINO-3-HYDROXYHEXANE

This is a division of U.S. patent application Ser. No. 08/281,502, filed Jul. 27, 1994, now U.S. Pat. No. 5,491,253 which is a continuation-in-part of U.S. patent application Ser. No. 8/141,795, filed Oct. 22, 1993 now abandoned.

TECHNICAL FIELD

The present invention relates to intermediates and processes which are useful for the preparation of a substituted 2,5-diamino-3-hydroxyhexane.

BACKGROUND OF THE INVENTION

Compounds which are inhibitors of HIV protease are useful for inhibiting HIV protease in vitro and in vivo and are useful for inhibiting an HIV infection. Certain HIV protease inhibitors comprise a moiety which is a substituted 2,5-diamino- 3-hydroxyhexane. HIV protease inhibitors of particular interest are compounds of the formula 1:

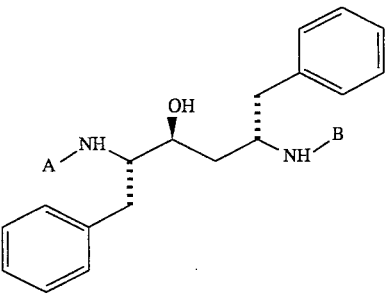

1 wherein A is $R_2NHCH(R_1)C(O)$— and B is $R_{2a}$ or wherein A is $R_{2a}$ and B is $R_2NHCH(R_1)C(O)$— wherein $R_1$ is loweralkyl and $R_2$ and $R_{2a}$ are independently selected from —C(O)—$R_3$—$R_4$ wherein at each occurrence $R_3$ is independently selected from O, S and —N($R_5$)— wherein $R_5$ is hydrogen or loweralkyl and at each occurrence $R_4$ is independently selected from heterocyclic or (heterocyclic)alkyl; or a pharmaceutically acceptable salt, prodrug or ester thereof. Compounds of formula 1 are disclosed in European Patent Application No. EP0486948, published May 27, 1992.

A preferred HIV protease inhibitor of formula 1 is a compound of formula 2a:

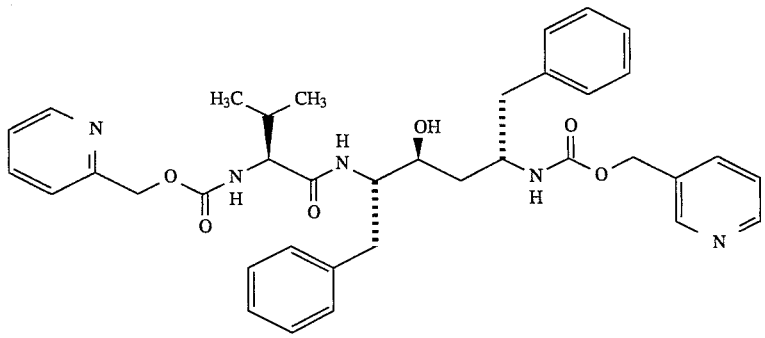

2a or a pharmaceutically acceptable salt, prodrug or ester thereof.

Another preferred HIV protease inhibitor of formula I is a compound of formula 2b:

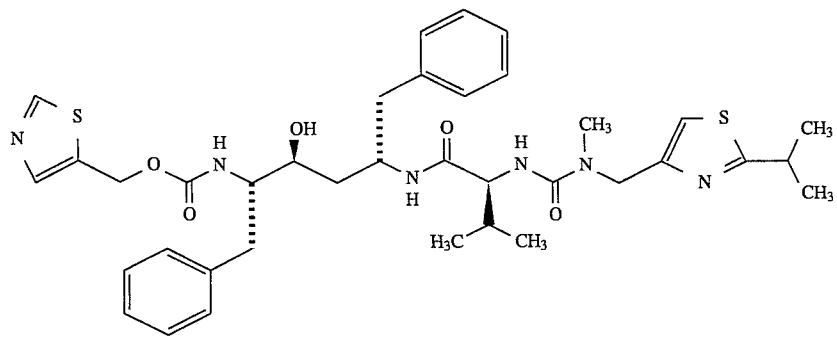

2b

The compound of formula 2b is disclosed in PCT Patent Application No. WO94/14436, published Jul. 7, 1994, which is hereby incorporated herein by reference.

An intermediate which is especially useful for preparing compounds of the formula 1 and 2 is a substantially pure compound of the formula 3:

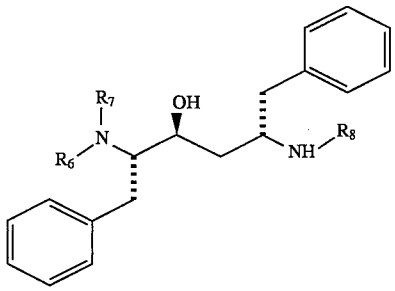

wherein $R_6$, $R_7$ and $R_8$ are independently selected from hydrogen and an N-protecting group; or an acid addition salt thereof. Preferred N-protecting groups $R_6$ and $R_7$ are independently selected from

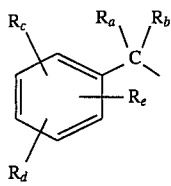

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

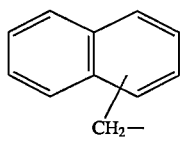

wherein the naphthyl ring is unsubstituted or substituted with one, two or three substitutents independently selected from loweralkyl, trifluoromethyl, alkoxy and halo.

Alternatively $R_6$ and $R_7$ taken together with the nitrogen atom to which they are bonded are

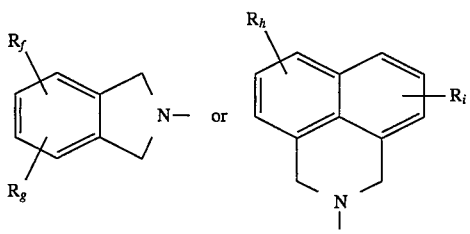

wherein $R_f$, $R_g$, $R_h$ and $R_i$ are independently selected from hydrogen, loweralkyl, alkoxy, halogen and trifluoromethyl.

In addition, $R_7$ can be $R_{7a}OC(O)$— wherein $R_{7a}$ is loweralkyl (preferably, t-butyl) or benzyl.

More preferred N-protecting groups $R_6$ and $R_7$ are those wherein $R_6$ and $R_7$ are independently selected from benzyl and substituted benzyl wherein the phenyl ring of the benzyl group is substituted with one, two or three substituents independently selected from loweralkyl, trifluoromethyl, alkoxy, halo and phenyl. The most preferred N-protecting groups $R_6$ and $R_7$ are those wherein $R_6$ and $R_7$ are each benzyl.

Preferred N-protecting groups $R_8$ are —C(O)R" wherein R" is loweralkyl, alkoxy, benzyloxy or phenyl wherein the phenyl ring is unsubstituted or substituted with one, two or three substituents independently selected from loweralkyl, trifluoromethyl, alkoxy and halo. A most preferred N-protecting group $R_8$ is t-butyloxycarbonyl.

Preferred intermediates of the formula 3 are the compounds wherein (i) $R_6$, $R_7$ and $R_8$ are each hydrogen or (ii) $R_6$ and $R_7$ are each benzyl or substituted benzyl wherein the phenyl ring of the benzyl group is substituted with one, two or three substituents independently selected from loweralkyl, trifluoromethyl, alkoxy, halo and phenyl, or $R_6$ and $R_7$ taken together with the nitrogen atom to which they are bonded are

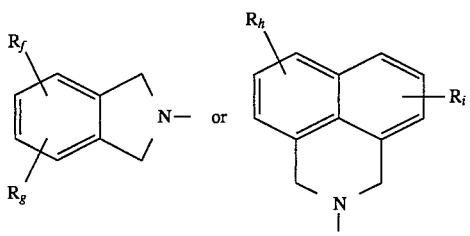

wherein $R_f$, $R_g$, $R_h$ and $R_i$ are independently selected from hydrogen, loweralkyl, alkoxy, halogen and trifluoromethyl and $R_8$ is hydrogen or t-butyloxycarbonyl or (iii) $R_6$ and $R_7$ are hydrogen and $R_8$ is t-butyloxycarbonyl.

DISCLOSURE OF THE INVENTION

The present invention relates to intermediates and processes for the preparation of a substantially pure compound of the formula 3. A key intermediate in the processes of the present invention is a substantially pure compound of the formula 4:

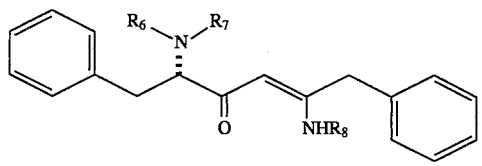

wherein $R_6$ and $R_7$ are independently selected from

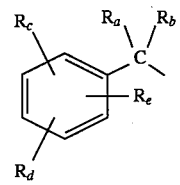

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

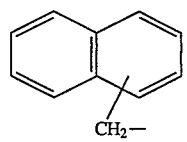

wherein the naphthyl ring is unsubstituted or substituted with one, two or three substitutents independently selected from loweralkyl, trifluoromethyl, alkoxy and halo; or $R_6$ is as defined above and $R_7$ is $R_{7a}OC(O)$— wherein $R_{7a}$ is loweralkyl or benzyl; or $R_6$ and $R_7$ taken together with the nitrogen atom to which they are bonded are

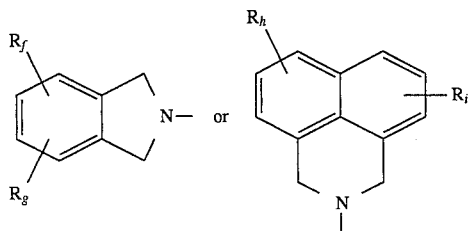

wherein $R_f$, $R_g$, $R_h$ and $R_i$ are independently selected from hydrogen, loweralkyl, alkoxy, halogen and trifluoromethyl and $R_8$ is hydrogen or —C(O)R" wherein R" is loweralkyl, alkoxy, benzyloxy or phenyl wherein the phenyl ring is unsubstituted or substituted with one, two or three substituents independently selected from loweralkyl, trifluoromethyl, alkoxy and halo; or an acid addition salt thereof.

A preferred intermediate is the compound of formula 4 wherein $R_6$ and $R_7$ are independently selected from benzyl and substituted benzyl wherein the phenyl ring of the benzyl group is substituted with one, two or three substituents independently selected from loweralkyl, trifluoromethyl, alkoxy, halo and phenyl and $R_8$ is hydrogen or —C(O)R" wherein R" is loweralkyl, alkoxy or phenyl wherein the phenyl ring is unsubstituted or substituted with one, two or three substituents independently selected from loweralkyl, trifluoromethyl, alkoxy and halo.

A more preferred intermediate is the compound of the formula 4 wherein $R_6$ and $R_7$ are benzyl and $R_8$ is hydrogen or t-butyloxycarbonyl.

Another key intermediate in the processes of the present invention is a substantially pure compound of the formula 6:

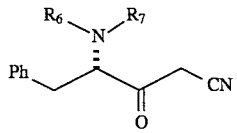 6 wherein $R_6$ and $R_7$ are independently selected from

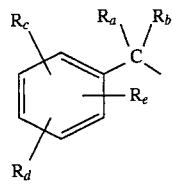 (i)

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

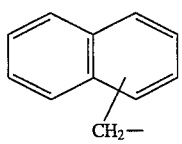 (ii)

wherein the naphthyl ring is unsubstituted or substituted with one, two or three substitutents independently selected from loweralkyl, trifluoromethyl, alkoxy and halo; or
$R_6$ is as defined above and $R_7$ is $R_{7a}OC(O)$— wherein $R_{7a}$ is loweralkyl or benzyl; or
$R_6$ and $R_7$ taken together with the nitrogen atom to which they are bonded are

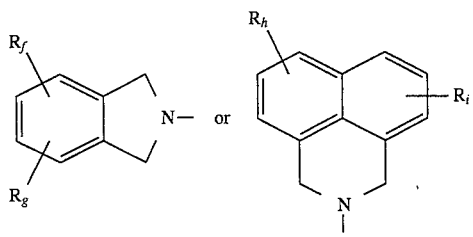

wherein $R_f$, $R_g$, $R_h$ and $R_i$ are independently selected from hydrogen, loweralkyl, alkoxy, halogen and trifluoromethyl; or an acid addition salt thereof.

A preferred intermediate is the compound of formula 6 wherein $R_6$ and $R_7$ are independently selected from benzyl and substituted benzyl wherein the phenyl ring of the benzyl group is substituted with one, two or three substituents independently selected from loweralkyl, trifluoromethyl, alkoxy, halo and phenyl.

A more preferred intermediate is the compound of the formula 6 wherein $R_6$ and $R_7$ are benzyl.

A process for the preparation of 4 and 6 is shown in Scheme I. N-protection of L-phenylalanine (for example, $R_6$ and $R_7$ are both benzyl) and esterification (for example, R is loweralkyl or benzyl) provides compound 5. Reaction of 5 with the α-carbanion of acetonitrile in an inert solvent provides nitrile 6. Suitable inert solvents include ethereal solvents (for example, tetrahydrofuran (THF), dimethoxyethane (DME), methyl tert-butyl ether (MTBE), diethyl ether and the like) or a mixture of an ethereal solvent and a hydrocarbon solvent (for example, pentane, hexane, heptane and the like). A preferred solvent is a THF/heptane mixture. The α-carbanion of acetonitrile can be prepared by reacting acetonitrile with bases such as sodium amide, potassium t-butoxide, sodium hexamethyldisilazane, sodium hydride, lithium diisopropylamide, lithium diethylamide, n-BuLi and the like. Alternatively, reaction of 5 with the enolate of tert-butyl cyanomalonate, followed by decarboalkoxylation, provides nitrile 6. Reaction of nitrile 6 with benzyl Grignard (for example, benzylmagnesium chloride) provides enamine 4.

A process for the preparation of 3 from 4 is shown in Scheme II. In the process of Scheme II, if $R_7$ is $R_{7a}OC(O)$—, then $R_{7a}$ is benzyl. Reaction of 4 with a borohydride reducing agent (for example, NaBH$_4$, NaBH$_3$CN, LiBH$_4$, KBH$_4$, K(OiPr)$_3$BH, Na(OMe)$_3$BH and the like) in the presence of a carboxylic acid ($R_{25}$—COOH wherein $R_{25}$ is loweralkyl, haloalkyl, phenyl or halophenyl) in an inert solvent in a molar ratio of enamine:reducing agent:carboxylic acid of 1: from about 1 to about 20: from about 1 to about 20 provides 7 (i.e., 3a wherein $R_8$ is hydrogen). A preferred reducing agent is NaCNBH$_3$ and a preferred carboxylic acid is trifluoroacetic acid. A preferred ratio of enamine:reducing agent:carboxylic acid is 1:about 4:about 4. In this process, the reducing agent is added to a solution of the enamine, followed by addition of the carboxylic acid.

An alternative process for the preparation of 3 from 4 involves a one-pot 2-step reaction sequence. In the first step of this alternative process, the enamine is reacted with a boron-containing reducing agent wherein the reducing agent has first been reacted with an acid selected from (i) $R_{26}$—COOH wherein $R_{26}$ is loweralkyl, haloalkyl, phenyl or halophenyl, (ii) $R_{27}$—SO$_3$H wherein $R_{27}$ is OH, F, loweralkyl, haloalkyl, phenyl, loweralkyl-substituted phenyl, halophenyl or naphthyl and (iii) $R_{28}$—PO$_3$H$_2$ wherein $R_{28}$ is OH, loweralkyl or phenyl or a combination of said acids.

Examples of boron-containing reducing agents include borohydride reducing agents (for example, NaBH$_4$, NaCNBH$_3$, LiBH$_4$, KBH$_4$ and the like), boron-containing reducing agents such as 9-borabicyclo[3.3.1]nonane, (R)-B-isopinocampheyl- 9-borabicyclo[3.3.1 ]nonane or (S)-B-isopinocampheyl-9borabicyclo[3.3.1 ]nonane and the like, and BH$_3$ complexes such as borane amine complexes (for example, borane-ammonia complex, borane-t-butylamine complex, borane-N,N-diethylaniline complex, borane-N,N-diisopropyl-ethylamine complex, borane-dimethylamine complex,4-(borane-dimethylamino)pyridine, borane-4-ethylmorpholine complex, borane-2,6-lutidine complex, borane-4-methylmorpholine complex, borane-morpholine complex, borane-4-phenylmorpholine complex, borane-piperazine complex, borane-piperidine complex, borane-poly(2-vinylpyridine) complex, borane-pyridine complex, borane-pyrrole complex, borane-trimethylamine complex, borane-triethylamine complex and the like), borane ether complexes (for example, borane-tetrahydrofuran complex and the like), a borane sulfide complex (for example, borane-methylsulfide complex, borane-1,4-oxathiane and the like) and borane phosphine complexes (for example, borane-tributylphosphine complex, borane-triphenylphosphine complex and the like) and the like.

A preferred boron-containing reducing agent is a borohydride reducing agent. A preferred borohydride reducing agent is NaBH$_4$.

Examples of acids R$_{26}$—COOH include acetic acid, propionic acid, trifluoroacetic acid, trichloroacetic acid, dichloroacetic acid, difluoroacetic acid, benzoic acid and pentafluorobenzoic acid. Examples of acids R$_{27}$—SO$_3$H include sulfuric acid, methanesulfonic acid, ethanesulfonic acid, trifluoromethanesulfonic acid, fluorosulfonic acid, phenylsulfonic acid and p-toluenesulfonic acid. Examples of acids R$_{28}$—PO$_3$H$_2$ include phosphoric acid, methylphosphonic acid, ethylphosphonic acid and phenylphosphonic acid.

A preferred acid is R$_{27}$—SO$_3$H. A more preferred acid is methanesulfonic acid.

In the first step of the alternative process, the acid is added to the boron-containing reducing agent in an inert solvent. Then the enamine is added to the boron-containing reducing agent/acid complex. In the first step of the alternative process, the molar ratio of enamine: reducing agent: acid is 1:from about 1 to about 10:from about 2 to about 20.

In the first step of the alternative process, a preferred molar ratio of enamine:reducing agent:acid is 1:from about 2 to about 4:from about 4 to about 10. A most preferred molar ratio of enamine:reducing agent:acid is 1: about 2.5:about 6.

Suitable inert solvents for this process include alkyl- and aryl- ethers and polyethers such as tetrahydrofuran (THF), dimethoxyethane (DME), methyl tert-butyl ether (MTBE), diethyl ether and the like.

In the first step of the alternative process, before the enamine is added to the boron-containing reducing agent/ acid complex, a protic solvent (for example, isopropanol, ethanol, methanol, water and the like) can optionally be added to the boron-containing reducing agent/acid complex. Alternatively, the protic solvent can be mixed with the enamine before the enamine is added to the boron-containing reducing agent/acid complex. The protic solvent is added in an amount of from about 0 to about 10 molar equivalents (based on the enamine). A preferred protic solvent is isopropanol in the amount of about 7 molar equivalents.

The second step of the alternative process involves adding to the reaction mixture resulting from the first step (i.e., the reduction substrate) a complex of a borohydride reagent (for example, NaBH$_4$, LiBH$_4$, KBH$_4$, NaCNBH$_3$ and the like; preferably, NaBH$_4$) and a carboxylic acid (R$_{29}$—COOH wherein R$_{29}$ is loweralkyl, haloalkyl, phenyl or halophenyl) to provide 7 (i.e., 3 wherein R$_8$ is hydrogen). The borohydride reagent/carboxylic acid complex is prepared by adding the acid to the borohydride reagent in an inert solvent.

In the second step of the alternative process, the preferred carboxylic acid is trifluoroacetic acid. In the second step of the alternative process, the molar ratio of reduction substrate:borohydride reagent:carboxylic acid is 1: from about 1 to about 8: from about 1 to about 24. A preferred molar ratio of reduction substrate:borohydride reagent:carboxylic acid is 1: about 4: from about 4 to about 12. A most preferred molar ratio of reduction substrate:borohydride reagent:carboxylic acid is 1: about 4: about 5.

The second step of the alternative process can also be accomplished by adding to the reaction mixture resulting from the first step (i.e., the reduction substrate) a boron complexing agent such as mono-, di- or tri-ethanolamine, diaminoethane, diaminopropane, ethylene glycol, propylene glycol and the like, followed by the addition of a ketone reducing agent (for example, LiAlH$_4$, NaBH$_4$, NaBH$_3$CN, LiBH$_4$, KBH$_4$, K(OiPr)$_3$BH, Na(OMe)$_3$BH and the like; preferably,NaBH$_4$) as a solid or as a solution of the ketone reducing agent in an inert solvent to provide 7 (i.e., 3 wherein R$_8$ is hydrogen). Suitable inert solvents include dimethylformamide (DMF), dimethylacetamide, triglyme and the like.

In this version of the second step of the alternative process, the preferred boron complexing agent is triethanolamine and the preferred ketone reducing agent is NaBH$_4$. The molar ratio of reduction substrate: boron complexing agent:ketone reducing agent is 1: from about 3 to about 4: from about 2 to about 3. A preferred molar ratio of reduction substrate: boron complexing agent: ketone reducing agent is 1: about 3: about 2.5. A preferred solvent for the NaBH$_4$ solution is dimethylacetamide.

Compound 7 can be N-deprotected by hydrogenation (for example, with H$_2$ and Pd/C or H$_2$ and Pd(OH)$_2$ or formic acid and Pd/C or ammonium formate and Pd/C and the like) to provide the compound of formula 3b wherein R$_6$, R$_7$ and R$_8$ are each hydrogen.

Alternatively, the free 5-amino group of compound 7 can be N-protected (for example, as the t-butyloxycarbonylamino group by reaction with di-t-butyl dicarbonate or other activated t-butyloxycarbonyl esters or azides). The N-protecting groups on the 2-amino group can be selectively removed as described above to provide the compound of formula 3c wherein R$_6$ and R$_7$ are hydrogen and R$_8$ is an N-protecting group.

A preferred embodiment of the compound of formula 3c is the compound wherein R$_8$ is t-butyloxycarbonyl. A preferred method for isolating and purifying this compound involves crystallizing the compound as its salt with an organic carboxylic acid. Examples of suitable organic carboxylic acids include succinic acid, fumaric acid, malonic acid, glutaric acid, cinnamic acid, malic acid, mandelic acid, oxalic acid, tartaric acid, adipic acid, maleic acid, citric acid, lactic acid and the like.

Preferred carboxylic acids are succinic acid and fumaric acid.

Using one or the other of the N-protected forms of the compound of formula 3, it is possible to selectively further functionalize either the 2-amino group or the 5-amino group while the other amino group is N-protected.

An alternative method for preparing compound 7 from compound 4 is shown in Scheme III. In the process of Scheme III, if $R_7$ is $R_{7a}OC(O)$—, then $R_{7a}$ is loweralkyl. Reaction of 4 with $R_9ONH_2$ ($R_9$ is hydrogen, loweralkyl or benzyl) provides oxime 8. Reduction of the oxime 8 (for example, with $LiAlH_4$ and the like) provides 7.

An alternative process for the preparation of 3 from 4 is shown in Scheme IV. The free amino group of enamine 4 can be protected to give compound 9 (R" is phenyl, susbstituted phenyl, loweralkyl, benzyloxy or alkoxy). Preferably, $R_6$ and $R_7$ are each benzyl and R" is t-butyloxy. Reaction of 9 with a ketone reducing agent (for example, lithium aluminum hydride, lithium triethylborohydride or sodium borohydride and the like) gives the alcohol 10. Hydrogenation of 10 with hydrogen and a hydrogenation catalyst (for example, platinum oxide, palladium hydroxide on carbon or platinum on carbon and the like) provides di-N-protected 3. Selective N-deprotection of di-N-protected 3 provides a mono-N-protected 3a or 3c. Subsequent deprotection of the other amino group of the mono-N-protected 3a or 3c provides the unprotected diaminoalcohol 3b.

An alternative process for the preparation of 3 from 9 is shown in Scheme V. Reaction of 9 ($R_6$, $R_7$ and R" are defined as herein; preferably, $R_6$ and $R_7$ are benzyl and R" is t-butyloxy) with a boron-containing reducing agent such as 9-borabicyclo[3.3.1]nonane, (R)-B-isopinocampheyl-9borabicyclo[ 3.3.1]nonane or (S)-B-isopinocampheyl-9-borabicyclo[ 3.3.1 ]nonane and the like, borane solutions in complexing and noncomplexing solvents (for example, borane solutions in diethyl ether, methyl t-butyl ether, dioxane, dioxolane or methylene chloride and the like or mixtures thereof) or a $BH_3$ complex such as a borane ether complex (for example, borane-tetrahydrofuran complex and the like), a borane sulfide complex (for example, borane-methylsulfide complex, borane-1,4-oxathiane and the like), or a borane phosphine complex (for example, borane-tributylphosphine complex, borane-triphenylphosphine complex and the like) and the like) provides ketone 11. A preferred boron-containing reducing agent is borane-tetrahydrofuran complex. Reduction of ketone 11 with, for example, $LiAlH_4$, $NaBH_4$, $NaBH_3CN$, $LiBH_4$, $KBH_4$, $K(OiPr)_3BH$, $Na(OMe)_3BH$ and the like) provides di-N-protected 3. A preferred ketone reducing agent is $LiAlH_4$ or $KBH_4$.

SCHEME I

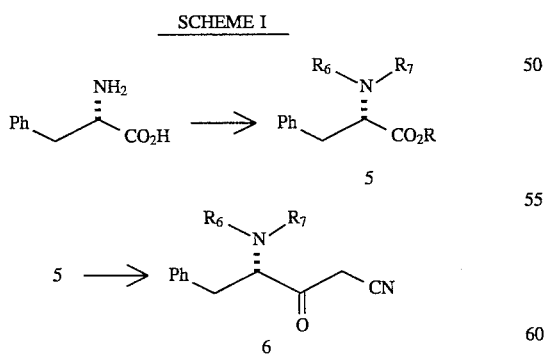

-continued
SCHEME I

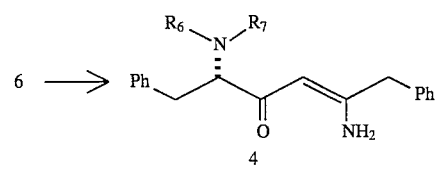

SCHEME II

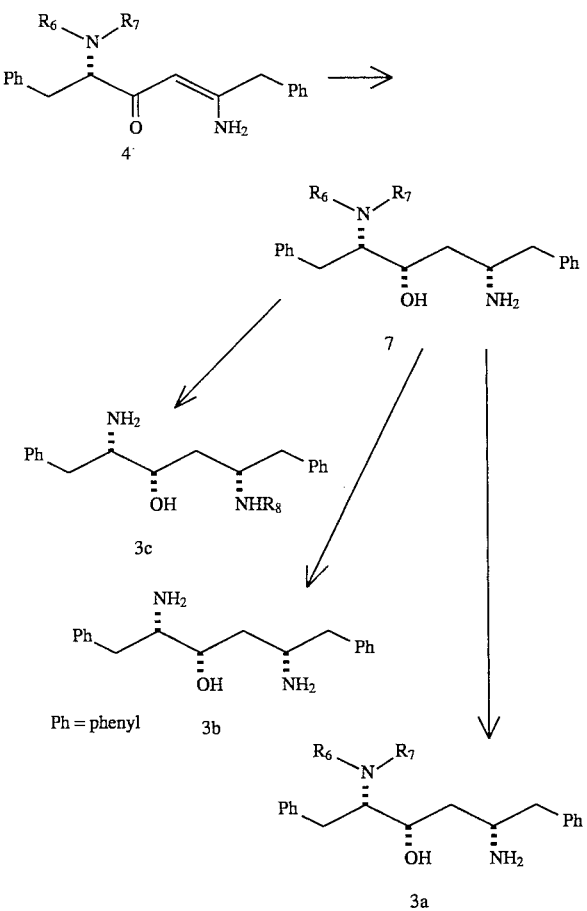

Ph = phenyl

SCHEME III

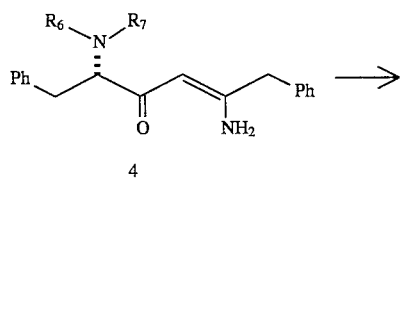

11
-continued
SCHEME III

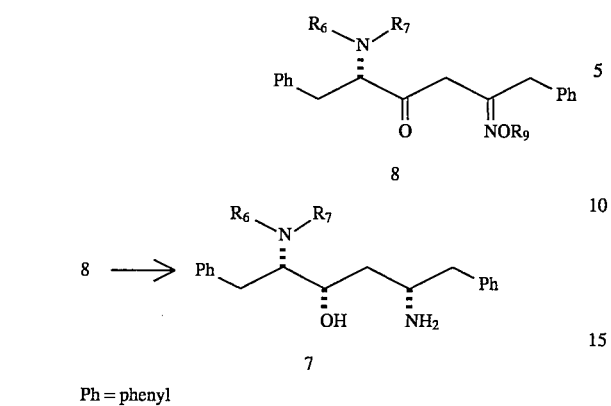

Ph = phenyl

SCHEME IV

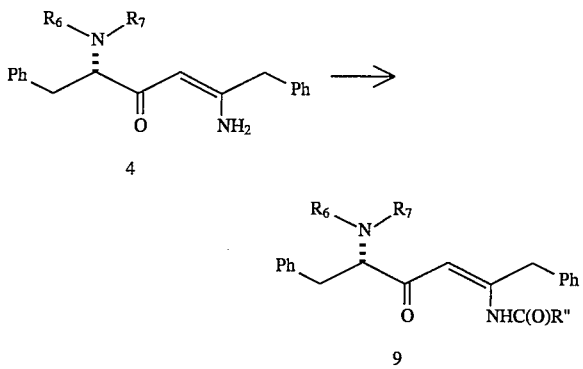

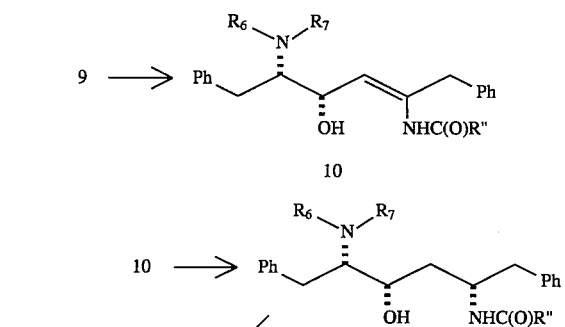

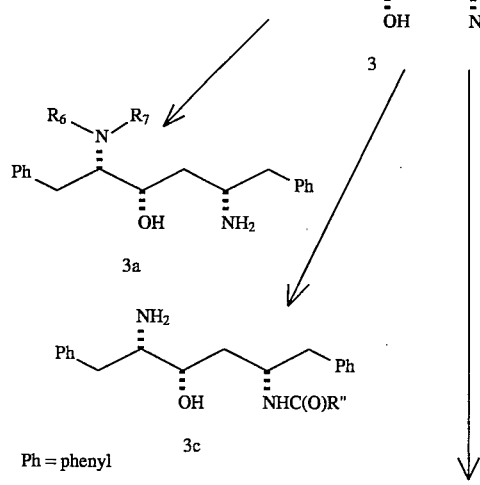

Ph = phenyl

12
-continued
SCHEME IV

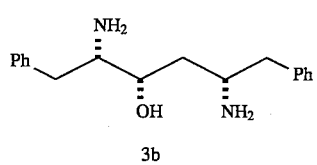

SCHEME V

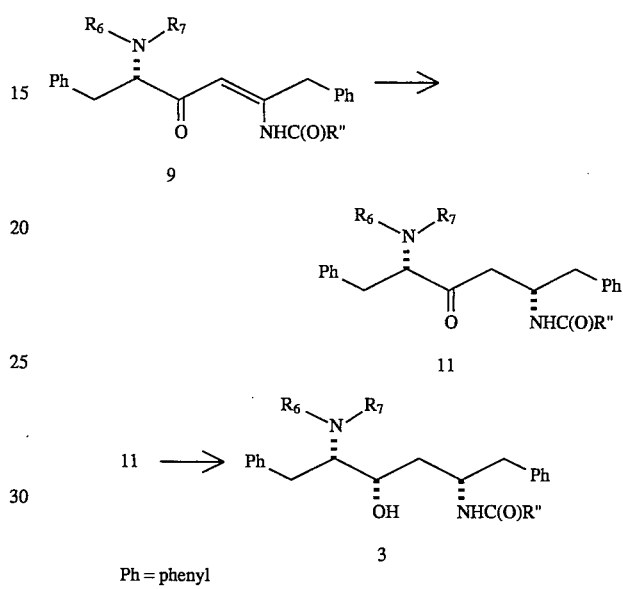

Ph = phenyl

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "alkoxy" as used herein refers to $-OR_{10}$ wherein $R_{10}$ is a loweralkyl group.

The term "halo" as used herein refers to F, Cl, Br or I.

The term "haloalkyl" as used herein refers to a loweralkyl group in which one or more hydrogen atoms has been replaced with a halogen including, but not limited to, trifluoromethyl, trichloromethyl, difluoromethyl, dichloromethyl, fluoromethyl, chloromethyl, chloroethyl, 2,2-dichloroethyl and the like.

The term "halophenyl" as used herein refers to a phenyl group in which one, two, three, four or five hydrogen atoms have been replaced with a halogen including, but not limited to, chlorophenyl, bromophenyl, fluorophenyl, iodophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,5-trichlorophenyl, 2,4,6-trichlorophenyl, 2-chloro-4-fluorophenyl, 2-chloro-6-fluorophenyl, 2,4-dichloro-5-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,5-trichlorophenyl, 2,4,6-trichlorophenyl, 2,3,4-trifluorophenyl, 2,3,6-trifluorophenyl, 2,4,5-trifluorophenyl, 2,4,6-trifluorophenyl, 3,4,5-trifluorophenyl, 2,3,4,5-tetrafluorophenyl, 2,3,5,6-tetrafluorophenyl, pentafluorophenyl and the like.

Acid addition salts of the compounds of the invention can be derived from reaction of an amine-containing compound of the invention with an inorganic or organic acid. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, malonate, glutarate, malate, mandelate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate.

Examples of acids which may be employed to form acid addition salts include such inorganic acids as hydrochloric acid, sulphuric acid and phosphoric acid and such organic acids as oxalic acid, maleic acid, succinic acid and citric acid, as well as the other acids mentioned above.

The term "substantially pure" as used herein refers to a compound which is contaminated by not more than 10% of any other stereoisomer (enantiomer or diastereomer), preferably by not more than 5% of any other stereoisomer and most preferably by not more than 3% of any other stereoisomer.

As used herein, the terms "S" and "R" configuration are as defined by the IUPAC 1974 Recommendations for Section E, Fundamental Stereochemistry, Pure Appl. Chem. (1976) 45, 13–30.

The following examples will serve to further illustrate the compounds and processes of the invention.

EXAMPLE 1

(L)-N,N-Dibenzylphenylalanine benzyl ester

A solution containing L-phenylalanine (161 kg, 975 moles), potassium carbonate (445 kg, 3220 moles), water (675 L), ethanol (340 L), and benzyl chloride (415 kg, 3275 moles) was heated to 90°±15° C. for 10–24 hours. The reaction mixture was cooled to 60° C. and the lower aqueous layer was removed. Heptane (850 L) and water (385 L) were added to the organics, stirred, and the layers separated. The organics were then washed once with a water/methanol mixture (150 L/150 L). The organics were then stripped to give the desired product as an oil, which was carried on in the next step without purification.

IR (neat) 3090, 3050, 3030, 1730, 1495, 1450, 1160 cm$^{-1}$, $^1$H NMR (300 MHz, CDCl$_3$) δ 7.5–7.0 (m, 20H), 5.3 (d, 1H, J=13.5 Hz), 5.2 (d, 1 H, J=13.5 Hz), 4.0 (d, 2H, J=15 Hz), 3.8 (t, 2H, J=8.4 Hz), 3.6 (d, 2H, J=15 Hz), 3.2 (dd, 1 H,J=8.4, 14.4 Hz), $^{13}$C NMR (300 MHz, CDCl$_3$) δ 172.0, 139.2, 138.0, 135.9, 129.4, 128.6, 128.5, 128.4, 128.2, 128.1, 128.1, 126.9, 126.2; 66.0, 62.3, 54.3, 35.6. [α]$_D$–79° (c=0.9, DMF).

EXAMPLE 2a

4-S-N,N-Dibenzylamino-3-oxo,5-phenyl-pentanonitrile

A solution containing the product of Example 1 (i.e., benzyl ester) (approx. 0.45 moles) in 520 mL tetrahydrofuran and 420 mL acetonitrile was cooled to −40° C. under nitrogen. A second solution containing sodium amide (48.7 g, 1.25 moles) in 850 mL tetrahydrofuran was cooled to −40° C. To the sodium amide solution was slowly added 75 mL acetonitrile and the resulting solution was stirred at −40° C. for more than 15 minutes. The sodium amide/acetonitrile solution was then slowly added to the benzyl ester solution at −40° C. The combined solution was stirred at −40° C. for one hour and then quenched with 1150 mL of a 25% (w/v) citric acid solution. The resulting slurry was warmed to ambient temperature and the organics separated. The organics were then washed with 350 mL of a 25% (w/v) sodium chloride solution, then diluted with 900 mL heptane. The organics were then washed three times with 900 mL of a 5% (w/v) sodium chloride solution, two times with 900 mL of a 10% methanolic water solution, one time with 900 mL of a 15% methanolic water solution, and then one time with 900 mL of a 20% methanolic water solution. The organics were stripped and the resulting material dissolved into 700 mL of hot ethanol. Upon cooling to room temperature, the desired product precipitated. Filtration gave the desired product in 59% yield from the L-phenylalanine. IR (CHCl$_3$) 3090, 3050, 3030, 2250, 1735, 1600, 1490, 1450, 1370, 1300, 1215 cm$^{-1}$, $^1$H NMR (CDCl$_3$) δ 7.3 (m, 15H), 3.9 (d, 1H, J=19.5 Hz), 3.8 (d, 2H, J=13.5 Hz), 3.6 (d, 2H, J=13.5 Hz), 3.5 (dd, 1H, J=4.0, 10.5 Hz), 3.2 (dd, 1H, J=10.5, 13.5 Hz), 3.0 (dd, 1H, J=4.0, 13.5 Hz), 3.0 (d, 1H, J=19.5 Hz), $^{13}$C NMR (300 MHz, CDCl$_3$) δ 197.0, 138.4, 138.0, 129.5, 129.0, 128.8, 128.6, 127.8, 126.4, 68.6, 54.8, 30.0, 28.4. [α$_D$–95° (c=0.5, DMF).

EXAMPLE 2b

Alternate Preparation of 4-S-N,N-Dibenzylamine-3-oxo-5-phenyl-pentanonitrile

To a flask was charged sodium amide (5.8 g, 134 mmol) under nitrogen followed by 100 mL of methyl t-butyl ether (MTBE). The stirred solution was cooled to 0° C. Acetonitrile (8.6 mL, 165 mmol) was added over 1 minute. This solution was stirred at 5±5° C. for 30 minutes. A solution of (L)-N,N-dibenzylphenylalanine benzyl ester (25 g, 90% pure, 51.6 mmol) in 125 mL of MTBE was added over 15 minutes and the resulting heterogeneous mixture was stirred at 5±5° C. until the reaction was complete (approx. 3 hours). The reaction was quenched with 100 mL of 25% w/v aqueous citric acid and warmed to 25° C. before separating the layers. The organics were then washed with 100 mL of H$_2$O. The aqueous layer was separated and the organics filtered and concentrated in vacuo. The residue was crystallized from 50 mL of ethanol to afford 13.8 g of the desired product as a white solid.

EXAMPLE 2c

Alternate Preparation of 4-S-N,N-Dibenzylamino-3-oxo-5-phenyl-pentanonitrile

To a solution containing sodium amide (120 kg, 3077 moles), heptane (1194 L), and tetrahydrofuran (590 L) cooled to 0° C., was added a solution containing the product of Example 1 (i.e., benzyl ester) (approx. 975 moles), tetrahydrofuran (290 L), heptane (570 L), and acetonitrile (114 L). The addition was done maintaining the temperature below 5° C. The combined solution was stirred at 0±5° C for approx. one hour before quenching with 25% citric acid solution (1540 L) to adjust the pH to 5.0–7.0. The upper organic layer was separated and washed with 25% aqueous sodium chloride (715 kg), treated with activated carbon (2 kg), and stripped. The resulting residue was crystallized from a 55° C. ethanol/water solution (809 kg/404 kg). The solution was cooled to 0° C. prior to crystallizing to give approx. 215 kg of the desired product.

EXAMPLE 3

Alternate Preparation of
4-S-N,N-Dibenzylamino-3-oxo-5-phenyl-pentanonitrile

To a 1 liter jacketed reaction flask equipped with thermometer, nitrogen inlet, pressure-equalized addition funnel and mechanical stirrer was charged a solution of potassium t-butoxide (32 g, 0.289 mol, 3.0 equiv) in tetrahydrofuran (350 mL) and cooled to an internal temperature of −10° C. To this was added a solution of the product of Example 1 (i.e, benzyl ester) (42.0 g, 0.0964 mol, 1.0 equiv) in tetrahydrofuran (10 mL) and acetonitrile (15 mL, 0.289 mol, 3.0 equiv) via pressure-equalized addition funnel over a period of 20 minutes. During the addition, the internal temperature increased to −5° C. The reaction (now orange and transparent) mixture stirred an additional 30 min at −10° C. An aliquot removed from the reaction mixture after the addition of the benzyl ester solution was quenched in 10% aqueous citric acid and partitioned between heptane was analyzed by HPLC and revealed no starting material remained and the presence of the desired nitrile in 93% ee in favor of the S isomer, Chiralpak AD column, 1 mL/min,. 10%/-propanol in heptane, monitored @205 nm). The contents of the reactor were allowed to warm to 0° C. over 30 minutes. Citric acid (10% aqueous, 200 mL) was charged followed by Heptane (100 mL) and the reaction contents allowed to warm to 20° C. The aqueous phase was separated and the organic phase-was washed with 10% aqueous sodium chloride solution (200 mL) and the aqueous phase separated. The organic phase was concentrated in vacuo using a 45° C. bath. n-Butanol (100 mL) was then charged and distillation in vacuo was conducted until the contents were reduced by approximately 10% by volume. The suspension resulting was allowed to cool to 20° C. with mechanical stirring and held at that temperature for 18 hours. The solid was filtered and dried in vacuo at 45° C. The yield of the first crop was 20.5 g (57%). The material was >98% pure by HPLC.

EXAMPLE 4

2-Amino-5-S-N,N-dibenzylamino-4-oxo-1,6-diphenylhex-2-ene

To a −5° C. solution of the nitrile product of Example 2 (90 Kg, 244 moles) in tetrahydrofuran (288 L), was added benzylmagnesium chloride (378 Kg, 2M in THF, 708 moles). The solution was warmed to ambient temperature and stirred until analysis showed no starting material. The solution was then recooled to 5° C. and slowly transferred to a solution of 15% citric acid (465 kg). Additional tetrahydrofuran (85 L) was used to rinse out the original container and the rinse was added to the citric acid quench container. The organics were separated and washed with 10% sodium chloride (235 kg) and stripped to a solid. The product was stripped again from ethanol (289 L) and then dissolved in 80° C. ethanol (581 L)). After cooling to room temperature and stirring for 12 hours, the resulting product was filtered and dried in a vacuum oven at 30° C. to give approx. 95 kg of the desired product. mp 101°–102° C., IR (CDCl$_3$) 3630, 3500, 3110, 3060, 3030, 2230, 1620, 1595, 1520, 1495, 1450 cm$^{-1}$, $^1$H NMR (300 MHZ, CDCl$_3$) d 9.8 (br s, 1H), 7.2 (m, 20H), 5.1 (s, 1H), 4.9 (br s, 1H), 3.8 ( d, 2H, J=14.7 Hz), 3.6 (d, 2H, J=14.7 Hz), 3.5 (m, 3H), 3.2 (dd, 1 H, J=7.5, 4.4 Hz), 3.0 (dd, 1H, J=6.6, 14.4 Hz), $^{13}$C NMR (CDCl3) d 198.0, 162.8, 140.2, 140.1, 136.0, 129.5, 129.3, 128.9, 128.7, 128.1, 128.0, 127.3, 126.7, 125.6, 96.0, 66.5, 54.3, 42.3, 32.4. [α]$_D$−147° (c=0.5, DMF).

EXAMPLE 5a (2S, 3S, 5S)-5-Amino-2-N,N-dibenzylamino-3-hydroxy-1,6-diphenyl-hexane A. A suspension of sodium borohydride (6.6 kg, 175 moles) in tetrahydrofuran (157 L) was cooled to less than −10±5° C. Methanesulfonic acid (41.6 kg, 433 moles) was slowly added and the temperature kept below 0° C. during the addition. Once the addition was complete, a solution of water (6 L, 33 moles), the product of Example 4 (20 kg, 43 moles) and tetrahydrofuran (61 L) was slowly added while maintaining the temperature below 0° C. during the addition. The mixture was stirred for not less than 19 h at 0±5° C.

B. To a separate flask was added sodium borohydride (6.6 kg, 175 moles) and tetrahydrofuran (157 L). After cooling to −5±5° C., trifluoroacetic acid (24.8 kg, 218 moles) was added while maintaining the temperature below 15° C. The solution was stirred 30 min at 15°±5° C. and was then added to the reaction mixture resulting from step A, keeping the temperature at less than 20° C. This was stirred at 20±5° C. until reaction was complete. The solution was then cooled to 10±5° C. and quenched with 3N NaOH (195 kg). After agitating with tert-butyl methyl ether (162 L), the organic layer was separated and washed one time with 0.5N NaOH (200 kg), one time with 20% w/v aqueous ammonium chloride (195 kg), and two times with 25% aqueous sodium chloride (160 kg). The organics were stripped to give the desired product as an oil which was used directly in the next step.

IR (CHCl$_3$) 3510, 3400, 3110, 3060, 3030, 1630, $^1$H NMR (300 MHz, CDCl$_3$) δ 7.2 (m, 20H), 4.1 (d, 2H, J=13.5 Hz), 3.65 (m, 1H), 3.5 (d, 2H, J=13.5 Hz), 3.1 (m, 2H), 2.8 (m, 1H), 2.65 (m, 3H), 1.55 (m, 1H), 1.30 (m, 1H), 1.30 (m, 1H), $^{13}$C NMR (300 MHz, CDCl$_3$) δ 140.8, 140.1, 138.2, 129.4, 129.4, 128.6, 128.4, 128.3, 128.2, 126.8, 126.3,125.7, 72.0, 63.6, 54.9, 53.3, 46.2, 40.1, 30.2.

EXAMPLE 5b

Alternative Preparation of (2S, 3S, 5S)-5-Amino-2-N,N-dibenzylamino-3-hydroxy-1.6-diphenyl-hexane A suspension of sodium borohydride (30 kg, 793 moles) in 1,2-dimethoxyethane (1356 L) was cooled to less than −5° C. Methanesulfonic acid (192 kg, 1998 moles) was slowly added keeping the temperature below 5° C. Once the addition was complete, a solution of isopropanol (142 L, 1849 moles), the product of Example 4 (123 kg, 267 moles), and 1,2-dimethoxyethane (311 L) was slowly added to the borohydride solution maintaining the temperature below 5° C. during the addition. The mixture was stirred for not less than 12 h at 0±5° C.

The reaction was then quenched with the addition of triethanolamine (118 kg). The temperature of the reaction mixture was kept below 5° C. during the quench. A separate solution containing sodium borohydride (25 kg, 661 moles) and dimethylacetamide (184 kg) was then added while maintaining the temperature below 10° C. The solution was stirred for 3 hours at 10±5° C. The solution was then quenched with water (1375 L) and agitated for 30 minutes. After mixing with tert-butyl methyl ether (1096 L), the organic layer was separated and washed one time with 3% NaOH (443 kg), one time with 20% w/v aqueous ammonium chloride (1492 kg), and one time with 25% aqueous sodium chloride (1588 kg). The organics were stripped to give the desired product as an oil.

EXAMPLE 6

(2S, 3S, 5S)-2,5-Diamino-3-hydroxy-1,6-diphenylhexane dihydrochloride

To a stirred solution of [2S,3S ,5S]-2-N,N-dibenzylamino-3-hydroxy-5-amino- 1,6-diphenylhexane (20 kg, 43.1 mol) in methanol (250 kg) was added an aqueous solution of ammonium formate (13.6 kg, 215 mol) in water (23 kg) and an aqueous suspension of 5% wet palladium on carbon (4.0 kg, Degussa catalyst, E 101 NE/W, approximately 50–60% water by weight). The suspension which resulted was heated to reflux (70±10° C.) for 6 hours and then cooled to room temperature. The suspension was filtered through a bed of diatomaceous earth and the cake was washed with methanol (2×30 kg). The filtrate was concentrated via vacuum distillation to an aqueous oil. The aqueous residue was taken up in 1N NaOH (200 liters) and extracted with ethyl acetate (155 kg). The organic product layer was washed with a 20% aqueous sodium chloride solution (194 kg) and then with water (97 kg). The ethyl acetate product solution was then concentrated to an oil under vacuum distillation. Isopropanol (40 kg) was then charged to the residue and again the solution was concentrated to an oil with vacuum distillation. To the oil was charged isopropanol (160 kg) and concentrated aqueous hydrochloric acid (20.0 kg). The suspension/solution was then heated to reflux for 1 hour and then slowly cooled to room temperature. The slurry was then stirred for 12–16 hours. The slurry was filtered and the cake was washed with ethyl acetate (30 kg). The wet cake was resuspended in isopropanol (93 kg) and water (6.25 kg) and heated to reflux for 1 hour with stirring. The reaction mixture was then slowly cooled to room temperature and stirred for 12–16 hours. The reaction mixture was filtered and the wet cake was washed with isopropanol (12 kg). The solid was dried in a vacuum oven at 45° C. for approximately 24 hours to provide 7.5 kg of the desired product. $^1$H NMR (300 MHz, CD$_3$OD) δ 7.40–7.15 (m, 10H), 3.8 (ddd, 1H, J=11.4, 3.7, 3.7 Hz), 3.68–3.58 (m, 1H), 3.37 (ddd, 1H, J=7.5, 7.5, 3.5 Hz), 3.05–2.80 (m, 4H), 1.95–1.70 (m, 2H), $^{13}$C NMR (300 MHz, CD$_3$OD) δ 135.3, 135.1, 129.0, 128.9, 128.7, 128.7, 127.12, 127.07, 67.4, 57.1, 51.6, 38.4, 35.5, 35.2.

EXAMPLE 7

[2S,3S,5S]-2-N,N-dibenzylamino-3-hydroxy-5-t-butyloxycarbonylamino-1,6-diphenylhexane To a solution of the [2S,3S,5S]-2-N,N-dibenzylamino-3-hydroxy-5-amino- 1,6-diphenylhexane (approx. 105 kg, 226 moles) in MTBE (1096 L), was added BOC Anhydride (65 kg, 373 moles) and 10% potassium carbonate (550 kg). This mixture was stirred until reaction was complete (approx. 1 hour). The bottom layer was removed and the organics were washed with water (665 L). The solution was then stripped to give the desired product as an oil. 300 MHz $^1$H NMR (CDCl$_3$) δ 1.40 (s,9H), 1.58 (s, 2H), 2.45–2.85 (m, 4H), 3.05 (m, 1 H), 3.38 (d, 2H), 3.6 (m, 1H), 3.79 (m, 1H), 3.87 (d, 2H), 4.35 (s, 1H), 4.85 ) s, broad, 1H), 7.0–7.38 (m, 20 H).

EXAMPLE 8a

[2S, 3S 5S]-2-amino-3-hydroxy-5-t-butyloxycarbonylamino-1,6-diphenylhexane

To a stirred solution of [2S,3S,5S]-2-N,N-dibenzylamino-3-hydroxy-5-t-butyloxycarbonylamino- 1,6-diphenylhexane (12 g, 21.3 mmol)in methanol (350 mL) was charged ammonium formate (8.05 g, 128 mmol, 6.0 eq) and 10% palladium on carbon (2.4 g). The solution was stirred under nitrogen at 60° C. for three hours and then at 75° C. for 12 hours. An additional amount of ammonium formate (6 g) and 10% palladium on carbon (1.5 g) was added as well as 1 mL of glacial acetic acid. The reaction was driven to completion within 2 hours at a reflux temperature. The reaction mixture was then cooled to room temperature and then filtered through a bed of celite. The filter cake was washed with methanol (75 mL) and the combined filtrates were concentrated under reduced pressure. The residue was taken up in 1N NaOH (300 mL) and extracted into methylene chloride (2×200 mL). The combined organic layers were washed with brine (250 mL) and dried over sodium sulfate. Concentration of the solution under reduced pressure provided the desired product as a light colored oil which slowly crystallized upon standing (5 g). Further purification of the product could be accomplished by flash chromatography (silica gel, 5% methanol in methylene chloride). 300 MHz $^1$H NMR (CDCl$_3$) δ 1.42 (s, 9H), 1.58 (m, 1H), 1.70 (m, 1H), 2.20 (s, broad, 2H), 2.52 (m, 1H), 2.76–2.95 (m, 4 H), 3.50 (m, 1H), 3.95 (m, 1H), 4.80 (d, broad, 1H), 7.15–7.30 (m, 10H).

EXAMPLE 8b

[2S,3S,5S]-2-amino-3-hydroxy-5-t-butyloxycarbonylamino-1.6-diphenylhexane succinate salt To a solution of [2S,3S,5S]-2-N,N-dibenzylamino-3-hydroxy-5-t-butyloxycarbonylamino- 1,6-diphenylhexane(approx. 127 kg, 225 moles) in methanol (437 L), was added a methanolic (285 L) slurry of 5% palladium on carbon (24 kg). To this was added a solution of ammonium formate (84 kg, 1332 moles) in methanol (361 L). The solution was heated to 75° C. for 6–12 hours and then cooled to room temperature. Solids were filtered from the reaction mixture using a filter coated with filteraid (Celite) and the methanol was stripped from the reaction mixture using heat and vacuum (up to 70° C.). The residue was dissolved in isopropyl acetate (4400 kg) with heat (40° C.) and then washed with a 10% sodium carbonate solution (725 kg), and finally with water (665 L). Both of the washes were performed at 40° C. to keep the product in solution. The solvent was removed under vacuum with heat (up to 70° C.). Isopropyl alcohol (475 L) was then added and stripped off to remove residual solvents. Isopropanol (1200 L) was added to the residue and stirred until homogeneous. To this solution was added a solution of succinic acid (15–40 kg) in isopropanol (1200 L). The solution jacket was heated to 70° C. to dissolve all of the solids and then allowed to slowly cool to room temperature and stir for 6 hours. The solution was then filtered to give the desired product as a white solid (55–80 kg).

mp: 145°–146 ° C. $^1$H NMR: (Me$_2$SO-d$_6$, 300 MHz) δ 0.97 (d, 3H, IPA), 1.20 (s, 9H), 1.57 (t, 2H), 2.20 (s, 2H, succinic acid), 2.55 (m, 2H), 2.66 (m, 2H), 2.98 (m, 1H), 3.42 (m, 1H), 3.70 (m, 1H), 3.72 (m, 1H, IPA), 6.60 (d, 1H, amide NH), 7.0–7.3 (m, 10 OH). $^1$H NMR: (CD$_3$OD, 300 MHz) δ 1.11 (d, 3H, J=7 Hz, IPA), 1.29 (s, 9H), 1.70 (m, 2H), 2.47 (s, 2H, succinic acid), 2.65 (m, 2H), 2.85 (m, 2H), 3.22 (m,1H), 3.64 (m, 1H), 3.84 (m, 1H), 7.05–7.35 (m, 10H).

In a similar manner, the following salts of [2S,3S,5S]-2-amino-3-hydroxy-5 -t-butyloxycarbonylamino-1,6-diphenylhexane were prepared.

[2S,3S,5S]-2-Amino-3-hydroxy-5-t-butyloxycarbonyl-amino-1.6-diphenylhexane, fumarate salt:

mp: 157°–159 ° C. $^1$H NMR: (Me$_2$SO-d$_{6, 300}$ MHz) d 0.98 (d, 8H, IPA), 1.20 (s, 9H), 1.57 (t, 2H), 2.65 (m, 2H), 2.71 (m, 2H), 3.01 (m, 1H), 3.43 (m, 1H), 3.68 (m, 1H), 3.72 (m 3H), 6.47 (s, 1H, fumaric acid), 6.57 (d, 1H, amide NH), 7.0–7.3 (m, 10H).

[2S,3S,5S]-2-Amino-3-hydroxy-5-t-butyloxycarbonyl-amino-1.6-diphenylhexane malonate salt:

mp: 150°–152 ° C. $^1$H NMR: (Me$_2$SO-d$_6$, 300 MHz) d 0.98 (d, 1H, IPA), 1.17 (s, 9H), 1.61 (m, 2H), 2.65 (m, 2H), 2.66 (s, 1H, malonic acid), 2.81 (m, 2H), 3.31 (m, 1H), 3.53 (m, 1H) 3.69 (m, 1H), 6.61 (d, 1H, amide NH), 7.0–7.3 (m, 10H). 13C NMR: (Me$_2$SO-d$_6$) d 28.2, 36.1, 38.5, 38.9, 39.8, 48.0, 54.6, 65.3, 77.3, 125.8, 126.7, 127.8, 128.5, 129.2, 129.3, 136.5, 138.8, 155.0, 171.5.

[2S,3S,5S]-2-Amino-3-hydroxy-5-t-butyloxycarbonyl-amino-1,6-diphenylhexane glutarate salt:

mp: 162°–164 ° C. $^1$H NMR: (Me$_2$SO-d$_6$, 300 MHz) d 0.98 (d, 6H, IPA), 1.21 (s, 9H), 1.55 (m, 2H), 1.63 (m, 1H, glutaric acid), 2.25 (t, 2H, glutaric acid), 2.49 (m, 2H), 2.67 (m, 2H), 2.84 (m, 1H), 3.39 (m, 1H), 3.72 (m, 1H), 3.73 (m, 1H), 6.59 (d, 1H), 7.0–7.3 (m, 10H). $^{13}$C NMR; (Me$_2$SO-d$_6$) d 25.5, 28.2, 34.0, 48.5, 55.4, 62.0, 68.6, 77.0, 125.6, 125.7, 127.8, 127.9, 129.1, 139.0, 139.5, 154.9, 174.5.

[2S,3S,5S]-2-Amino-3-hydroxy-5-t-butyloxycarbonyl-amino-1,6-diphenylhexane trans-cinnamate salt mp: 164°–165 ° C. $^1$H NMR; (Me$_2$SO-d$_6$ 300 MHz) d 1.21 (s, 9H), 1.57 (m, 2H), 2.52 (m, 2H), 2.59 (m, 2H), 2.90 (m, 1H), 3.41 (m, 1H), 3.70 (m, 1H), 6.47 (d, 1H, cinnamic acid), 6.59 (d, 1H), 7.0–7.3 (m, 12H), 7.33 (m, 3H), 7.42 (d, 1H, cinnamic acid), 7.59 (m 2H). $^{13}$C NMR: (Me$_2$SO-d$_6$) d 28.2, 48.3, 55.2, 68.3, 77.1, 101.8, 125.6, 125.8, 127.8, 128.2, 128.8, 129.2, 134.9, 139.1, 139.2, 141.5, 166.0, 168.3, 200.0.

[2S,3S,5S]-2-Amino-3-hydroxy-5-t-butyloxycarbonyl-amino-1,6-diphenylhexane L-malate salt:

mp:152°–154 ° C. $^1$H NMR: (Me$_2$SO-d$_6$, 300 MHz) d 0.99 (d, 3H, IPA), 1.20 (s, 9H), 2.24 (dd, 1H, L-Malic acid), 2.40 (d, 1H, L-Malic acid), 2.48–2.78 (m, 3H), 3.02 (m, 1H), 3.44 (m, 1H), 3.58 (m, 1H), 3.61 (m, 1H, IPA), 3.77 (dd, 1H, L-Malic acid), 6.60 (d, 1H, amide NH), 7.0–7.3 (m, 10H). $^{13}$C NMR: (Me$_2$SO-d$_6$) d 25.5, 28.2, 48.3, 55.1, 61.8, 65.5, 67.3, 77.0, 125.5,

[2S,3S,5S]-2-Amino-3-hydroxy-5-t-butyloxycarbonyl-amino-1,6-diphenylhexane S(+) mandelate salt mp: 165°–167 ° C.

[2S,3S,5S]-2-Amino-3-hydroxy-5-t-butyloxycarbonyl-amino-1,6-diphenylhexane R(–)mandelate salt mp: 173°–175° C.

[2S,3S,5S]-2-Amino-3-hydroxy-5-t-butyloxycarbonyl-amino-1,6-diphenylhexane oxalate salt mp: 201–202

[2S,3S,5S]-2-Amino-3-hydroxy-5-t-butyloxycarbonyl-amino-1,6-diphenylhexane oxalate dihydrate salt mp: 206°–208° C.

[2S,3S,5S]-2-Amino-3-hydroxy-5-t-butyloxycarbonyl-amino-1,6-diphenylhexane D-tartrate salt mp:187°–188° C.

EXAMPLE 9 syn-(2S)-2-(N,N-dibenzyl)amino-5-benzyloxyimino-1,6-diphenyl-3-oxo-hexane and anti-(2S)-2-(N,N-dibenzyl)amino-5-benzyloxyimino- 1,6-diphenyl-3-oxo-hexane A solution of 1.0 mg (2.17 mmol) of (2S)-2-(N,N-dibenzyl)amino-5-amino- 1,6-diphenyl-3-oxo-4-hexene and 347 mg of O-benzylhydroxylamine hydrochloride (2.17 mmol) in 50 ml of acetonitrile was refluxed under N$_2$ atmosphere for 1 h. After most of the acetonitrile was removed in vacuo, the residue was treated with 20 ml of saturated aqueous NaHCO$_3$ and extracted with four 20 ml portions of dichloromethane. The combined organic layers were dried over Na$_2$SO$_4$ and concentrated in vacuo to provide 1.24 g (100%) of the desired syn and anti mixture as a colorless oil. The syn-O-benzyloxime and anti-O-benzyloxime could be separated by silica gel chromatography using 50% dichloromethane in hexane.

syn-O-benzyl oxime: $^1$H NMR (CDCl$_3$) δ 2.85 (1H, dd, J=13.5, 4.5 Hz), 3.03 (1H, d, J=16.5 Hz), 3.07 (1H, dd, J=13.5, 8.7 Hz), 3.44 (2H, q$_{AB}$), 3.53 (1H, dd, J=9.2, 4.0 Hz), 3.55 (2H, d, J=13.8 Hz), 3.60 (1H, d, J=16.9Hz), 3.69 (2H, d, J=1 3.8 Hz), 4.93 (2H, q$_{AB}$), 6.97–7.32 (25H, m). Mass spectrum: (M+H)$^+$=567.

anti-0-benzyl oxime: $^1$H NMR (CDCl$_3$) δ2.87 (1H, dd, J=13.5, 4.2 Hz), 3.07 (1H, d, J=16.8 Hz), 3.08 (1H, dd, J=13.5, 8.7 Hz), 3.42 (1H, d, J=16.5 Hz), 3.46 (1H, dd, J=9.0, 4.5 Hz), 3.51 (2H, d, J=13.6 Hz), 3.60 (2H, q$_{AB}$), 3.70 (2H, d, J=13.6Hz), 5.04 (2H, s), 6.68–7.35 (25H, m). Mass spectrum: (M+H)$^+$= 567.

EXAMPLE 10

Alternative Preparation of (2S,3S,5S)-2-(N,N-dibenzyl)amino-5-amino-1,6-diphenyl- 3-hydroxyhexane A solution of 100 mg (0.176 mmol) of syn-(2S)-2-(N,N-dibenzyl)amino-5-benzyloxyimino- 1,6-diphenyl-3-oxo-hexane in 2 mL of tetrahydrofuran was treated with 0.882 ml (0.882 mmol) of 1M solution of lithium aluminium hydride in tetrahydrofuran at 0° C. The reaction mixture was then gradually warmed to ambient temperature and stirred for 15 h. The mixture was quenched with saturated aqueous Na$_2$SO$_4$ (0.25 ml) and the resulting precipitate was filtered off. The filtrate was concentrated and the residue was purified by silica gel chromatography using 2% methanol and 2% isopropylamine in dichloromethane to provide 76.3 mg (93%) of the desired (2S,3S,5S) compound and two isomers (2S,3R,5R and 2S,3S,5R) in the ratio of 9.6:1:0.7.

The reaction started from the syn and anti mixture gave the same products, with a diasteriomer ratio of 8.0:0.6:1.

EXAMPLE 11

(S)-2-t-butyloxycarbonylamino-5-N,N-dibenzylamino-1,6-diphenyl-4-oxo-2-hexene

To 9.21 gm (20 mmol) of the product of Example 4 and 0.37 gm (3 mmol) 4-N,N-dimethylaminopyridine in 100 ml of methyl tert-butylether was added via syringe pump a solution containing 4.80 gm (22 mmol) di-tert-butyl carbonate in the same solvent (25 ml) over a period of 6 h. An additional amount (3 ml) of methyl tert-butylether was then added to complete the addition. After stirring at room temperature for 18 h the reaction mixture was cooled with the aide of an ice water bath. The resultant solid was collected by suction filtration and washed with cold (0° C.) methyl tert-butylether and hexane and dried under vacuum to give 9.9 gm of crude material as a white solid. The material thus isolated was disolved in a minimal amount of dichloromethane and purified by flash chromatography on silica gel. Elution of the column with a mixture of hexane-ethyl acetate-dichloromethane (8:1:1) gave, after concentration of the appropriate fractions, 8.1 gm (72%) of the desired N-Boc vinylogous amide. Mp. 191°–193° C. $[\alpha]_D$ –183.7° (c=1.05, CHCl$_3$). $^1$H NMR (CDCl$_3$, δ): 11.68 (bs, 1H), 7.05–7.47 (m, 20H), 5.28 (s,1H), 4.27 (d, J=16 Hz, 1H), 4.02 (d, J=16Hz, 1H), 3.58 (m, 4H), 3.40 (m, 1H), 3.11 (m, 1H), 2.90 (m, 1H), 1.48 (s, 9H).

EXAMPLE 12

Alternate Preparation of (S)-2-t-butyloxycarbonylamino-5-N,N-dibenzylamino-1,6-diphenyl-4-oxo-2-hexene A suspension of (S)-2-Amino-5-dibenzylamino-1,6-diphenyl-4-oxo-2-hexene (100.0 g, 0.217 mol) in 15% ethyl acetate/hexanes (2 liters) under N$_2$ was warmed to about 40° C. The resulting solution was cooled to room temperature before adding 4.0 g (33 mmol) of N,N-dimethyl-4-aminopyridine and 49.7 g (0.228 mol) of di-tert-butyl dicarbonate. The reaction mixture was allowed to stir overnight at room temperature. (Ater approximately one hour, a white precipitate began to form.)

The suspension was filtered and the precipitate was washed with hexanes to afford the desired product as colorless crystals. TLC: 25% ethyl acetate/hexanes R$_f$ 0.38.

EXAMPLE 13

(2S,3S)-2-N,N-Dibenzylamino-5-t-butyloxycarbonyl-amino-3-hydroxy-1,6-diphenyl-hex-4-ene A 100 ml flask was equipped with magnetic stirrer and positive nitrogen pressure. The flask was charged with the product of Example 11 (1 g, 1.8 mmol) and anhydrous THF (10 ml). The solution was chilled to 0° C. A 1M solution of LiAlH$_4$ in THF (1.8 ml, 1.8 mmol) was added. The cold bath was removed and the reaction was stirred at room temperature. Reaction was 80–90% complete after addition of the LAH. The reaction was quenched using the Fieser workup (0.2 ml H$_2$O; 0.2 ml 15% NaOH; 0.6 ml H$_2$O). The organic solution of the product was dried over anhydrous sodium sulfate and evaporated to provide the desired product as a white foam (~70% yield). TLC: 25% EtOAc/hexane starting material Rf=0.55, product Rf=0.45. $^1$H-NMR (CDCl$_3$) δ 7.37–7.10 m 20H; 6.78 br s 1H; 4.62 d 1H; 4.50 s 1H; 4.18 dd 1H; 3.90 d 3.65 dd 2H; 3.40 d 2H; 3.00 m 2H; 2.77 m 1H; 1.48 s 9H.

EXAMPLE 14

Alternate Preparation of (2S, 3S)-2-N,N-Dibenzylamino-5-t-butyloxycarbonylamino-3-hydroxy-1,6-diphenyl-hex-4-ene To a solution of 200 mg (0.36 mmole) of 2S-dibenzylamino-3-oxo-5-t-butyloxycarbonylamino- 1,6-diphenyl-hex-4-ene in 8 mL of dry THF at –78° C. was added 1.4 mL of a 1M solution of lithium triethylborohydride. The solution was stirred at –78° C. for 1 h and quenched with water and extracted with ethyl acetate (3×50 mL). The organic layer was dried with anhydrous sodium sulfate and filtered. Concentration of the ethyl acetate solution in vacuo and purification of the crude residue by silica gel column chromatography (20% EtOAc/hexane) provided 125 mg of pure desired product and 65 mg of recovered starting material. 300 MHz $^1$H NMR (CDCl$_3$): δ 1.48 (s, 9H), 2.75 (m, 1H), 2.98 (m, 2H), 3.40 (d, J=12 Hz, 2H), 3.65 (AB q, J=15 Hz, 2H), 3.90 (d, J=12 Hz, 2H), 4.17 (m, 1H), 4.48 (s, 1H), 4.62 (d, J=6.5 Hz, 1H), 6.77 (br s, 1H), 7.10–7.35 (m, 20H).

EXAMPLE 15

(2S, 3S, 5S)-2-N,N-Dibenzylamino-5-t-butyloxycarbonyl-amino-3-hydroxy-1,6-diphenylhexane To a suspension of 50 mg of platinum oxide in 12 mL of ethanol was added 120 mg of the product of Example 14. The reaction mixture was shaken vigorously under a hydrogen pressure of approx. 60 psi using a Parr hydrogenation apparatus. After 15 h, the catalyst was filtered and washed with 30 mL of ethanol. Solvent of the combined ethanol solution was evaporated in vacuo and the residue purified by silica gel column chromatography (3% to 5% EtOAc/CH$_2$Cl$_2$) to provide 10 mg of recovered starting material and 78 mg of desired product (70%). 300 MHz $^1$H NMR (CDCl$_3$): δ 1.20 (m, 2H), 1.40 (s, 9 H), 2.55–2.80 (m, 4H), 3.05 (m, 1H), 3.47 (d, J=13.5 Hz, 2H), 3.60 (m, 1H), 3.80 (m, 1H), 3.90 (d, J=13.5 Hz, 2H), 4.35 (s, 1H), 4.85 (br s, 1H), 7.02–7.30 (m, 20H).

EXAMPLE 16

(2S, 3S, 5S)-2-Amino-3-hydroxy-5-t-butyloxycarbonylamino-1,6-diphenylhexane.

To a suspension of 100 mg of 10% palladium hydroxide on charcoal in 10 mL of isopropyl alcohol was added 73 mg of the product of Example 156. The mixture was shaken vigorously under a hydrogen pressure of approx. 60 psi using a Parr hydrogenation apparatus for 18 h. The catalyst was filtered off and washed with 50 mL of isopropyl alcohol. The solvent was evaporated in vacuo and the residue was purified by silica gel column chromatography (5% to 10% MeOH/CH$_2$Cl$_2$) to provide 36 mg of desired product (72%). 300 MHz $^1$H NMR (CDCl$_3$): d 1.42 (s, 9H), 1.58 (m, 1H), 1.70 (m, 1H), 2.20 (br s, 2H), 2.52 (m, 1H), 2.76–2.95 (m, 4H), 3.50 (m, 1H), 3.95 (m, 1H), 4.80 (br d, 1H), 7.15–7.30 (m, 10H). Mass spectrum: (M+H)$^-$=385.

EXAMPLE 17

Alternative Preparation of (2S, 3S, 5S)-2-N,N-Dibenzylamino-5-t-butyloxycarbonylamino-3-hydroxy- 1,6-diphenylhexane A solution of the product of Example 11 (5 g, 8.9 mmol) in dichloromethane (100 ml) and 1,4-dioxolane (100 ml) was cooled to between −10° and −15° C. and treated dropwise with 1M BH$_3$THF (26.7 ml, 26.7 mmol). The solution was stirred at this temperature for 3 hr. The clear solution was quenched with excess methanol (20 ml) and stirred at room temperature for 30 min. The solvent was removed in vacuo.

The white foam was dissolved in THF (75 ml) and cooled to −40° C. A solution of LAH (9 ml, 1M in THF, 9 mmol) was added dropwise. After 10 min. the solution was quenched with water followed by dilute aqueous HCl. The organics were removed and the aqueous layer extracted with ethyl acetate (3×20 ml). The combined organics were washed (saturated aqueous bicarbonate followed by brine), dried (Na$_2$SO$_4$), filtered and evaporated to afford 4.9 g (99%) of the desired product as a white foam.

Alternately, the white foam resulting from the BH$_3$THF reaction step was dissolved in MeOH (45ml), cooled to +3° C. and treated portionwise with KBH$_4$ (1.44 g, 26.7 mmol). After addition of the last portion of KBH$_4$ the reaction was stirred for an additional 4 hours at +4° to +5° C. The solution was concentrated by ½ the volume in vacuo, diluted with ¼ hexane-EtOAc (70 ml) and quenched (with cooling, maintain temp. <30° C.) by adding a 10% solution of KHSO$_4$ to pH=about 5. NaOH (15% aqueous) was added to pH=12–13. The insoluble salts were removed by filtration, and the filter cake washed 3 times with 7 ml ¼ hexane/EtOAc. The filtrate and washes were transferred to a separatory funnel, diluted with 15 ml hexane and 15 ml H$_2$O. The organics were removed and the aqueous layer was extracted once with 20 mls (¼) hexane-EtOAc. The combined organics were washed (saturated brine), dried (Na$_2$SO$_4$), filtered, and evaporated to afford 5.2 g of the desired product which was used without further purification in subsequent reactions. Rf 0.5 (25% EtOAc/hexane) $^1$H NMR (CDCl$_3$) δ 7.37–7.10 (m 20H); 6.78 (br. s, 1H); 4.62 (d, 1H); 4.50 (s, 1H); 4.18 (dd, 1H); 3.9 (d, 2H); 3.65 (dd, 2H); 3.40 (d, 2H); 3.00 (m, 2H); 2.77 (m, 1H); 1.39 (s, 9H). MS (EI) m/e565 (M+H).

EXAMPLE 18

Alternative Preparation of (2S, 3S, 5S)-2-Amino-3-hydroxy-5-t-butyloxycarbonylamino- 1,6-diphenylhexane.

A solution of the product from Example 17 (150 gms, 250 mmol) dissolved in absolute EtOH (2 liters) was treated with 10% Pd/C (18 gms, prewetted), followed by addition of ammonium formate (78.6 gms, 1.25 moles) dissolved in H$_2$O (200ml). The resulting mixture was stirred at reflux for 2.5 hours. The mixture was cooled to room temperature and filtered through a pad of infusorial earth (20 g). The filter cake was washed 3 times with EtOH (70 ml each). The filtrate was concentrated in vacuo. The residue was dissolved into EtOAc (1 L) and washed (1N NaOH, followed by H$_2$O, followed by brine), dried (Na$_2$SO$_4$), filtered and concentrated in vacuo to a constant weight of 95 gms. (99.2% of theory). The light yellow solid (91.5 gms of the 95 gms) was slurried in hot heptane (600 ml) (steam bath) and treated with isopropanol (45 ml), and swirled to effect solution. The solution was allowed to slowly cool to room temperature over 3 hours, kept at room temperature for 2 more hours and filtered. The filter cake was washed 10 times with ⅔ hexane-isopropanol (30 ml each) to give the desired product as an off-white finely crystalline solid which was dried to constant weight of 57.5 gms.

The crude product (20 gms) was recrystallized from hot 140 ml heptane/ 17 ml isopropanol. After letting the solution cool slowly to room temperature, the mixture was let stand at room temperature for 2 hours and then filtered. The filter cake was rinsed (5×15 ml (⅔) heptane/isopropanol) and dried to a constant weight of 18.5 gms.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of a substantially pure compound of the formula:

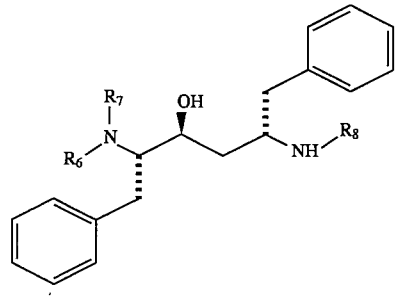

wherein R$_6$ and R$_7$ are each hydrogen or R$_6$ and R$_7$ are independently selected from

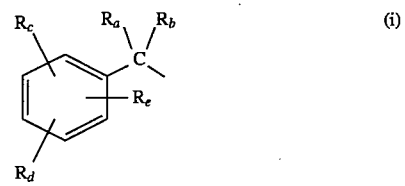

(i)

wherein R$_a$ and R$_b$ are independently selected from hydrogen, loweralkyl and phenyl and R$_c$, R$_d$ and R$_e$ are independently selected from hydrogen, loweralkyl, trifluoromethyl, alkoxy, halo and phenyl; and

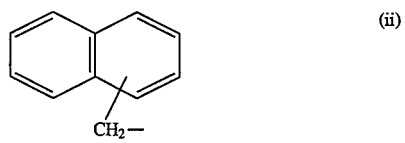

(ii)

wherein the naphthyl ring is unsubstituted or substituted with one, two or three substitutents independently selected from loweralkyl, trifluoromethyl, alkoxy and halo; or R$_6$ is as defined above and R$_7$ is R$_{7a}$OC(O)— wherein R$_{7a}$ is benzyl; or R$_6$ and R$_7$ taken together with the nitrogen atom to which they are bonded are

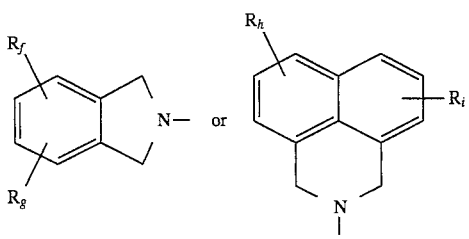

wherein $R_f$, $R_g$, $R_h$ and $R_i$ are independently selected from hydrogen, loweralkyl, alkoxy, halogen and trifluoromethyl and $R_8$ is hydrogen or —C(O)R" wherein R" is loweralkyl, alkoxy, benzyloxy or phenyl wherein the phenyl ring is unsubstituted or substituted with one, two or three substituents independently selected from loweralkyl, trifluoromethyl, alkoxy and halo; or an acid addition salt thereof comprising reacting a compound of the formula:

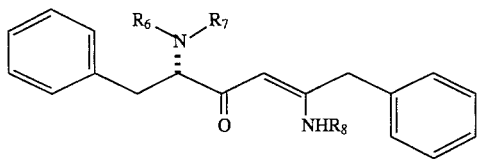

wherein $R_6$ and $R_7$ are each hydrogen or $R_6$ and $R_7$ are independently selected from

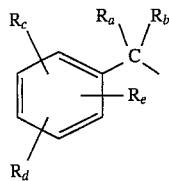 (i)

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

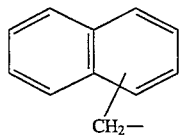 (ii)

wherein the naphthyl ring is unsubstituted or substituted with one, two or three substitutents independently selected from loweralkyl, trifluoromethyl, alkoxy and halo; or $R_6$ is as defined above and $R_7$ is $R_{7a}OC(O)$— wherein $R_{7a}$ is benzyl; or $R_6$ and $R_7$ taken together with the nitrogen atom to which they are bonded are

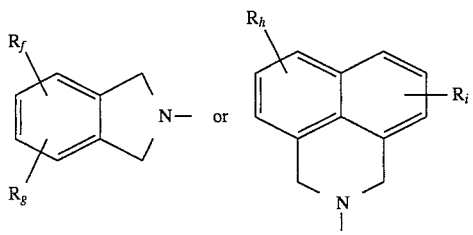

wherein $R_f$, $R_g$, $R_h$ and $R_i$ are independently selected from hydrogen, loweralkyl, alkoxy, halogen and trifluoromethyl and $R_8$ is hydrogen with a borohydride reducing agent, followed by the addition of $R_{25}$—COOH wherein $R_{25}$ is loweralkyl, haloalkyl, phenyl or halophenyl.

2. The process of claim 1 for the preparation of a substantially pure compound of the formula:

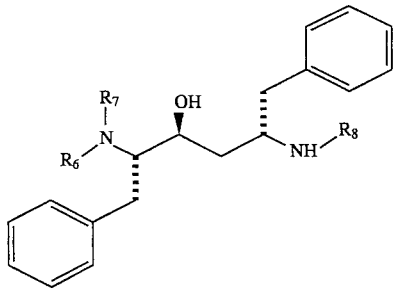

wherein $R_6$ and $R_7$ are each hydrogen or benzyl and $R_8$ is hydrogen or —C(O)R" wherein R" is t-butyloxy; or an acid addition salt thereof comprising reacting a compound of the formula:

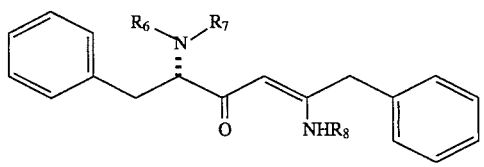

wherein $R_6$ and $R_7$ are each benzyl and $R_8$ is hydrogen with $NaCNBH_4$, followed by the addition of trifluoroacetic acid.

* * * * *